United States Patent [19]

Baker et al.

[11] Patent Number: 5,140,034

[45] Date of Patent: Aug. 18, 1992

[54] FIVE-MEMBERED RING SYSTEMS WITH BONDED IMIDAZOLYL RING SUBSTITUENTS

[75] Inventors: Raymond Baker, Much Hadham; Christopher Swain, Duxford; John Saunders, Bishops Standford, all of England

[73] Assignee: Merck Sharp & Dohme Ltd., Hertfordshire, England

[21] Appl. No.: 490,230

[22] Filed: Mar. 8, 1990

[30] Foreign Application Priority Data

Mar. 14, 1989 [GB] United Kingdom ............. 8905799.6
Jun. 27, 1989 [GB] United Kingdom ............. 8914732.6

[51] Int. Cl.$^5$ .................. C07D 413/14; A61K 31/41; A61K 31/42
[52] U.S. Cl. ................... 514/364; 514/324; 548/131; 548/235; 548/238; 548/239
[58] Field of Search ............... 548/131, 235, 238, 239; 514/364, 374

[56] References Cited

U.S. PATENT DOCUMENTS 4,914,207 4/1990 Nagel .................. 546/167
4,963,689 10/1990 Nagel .................. 548/181

OTHER PUBLICATIONS

*Chem. Ber.*, 1957, 90, 182.
*Synthesis*, 1975, 389.
*Advances in Heterocyclic Chemistry*, 1970, 12, 104.
*Nature*, 1985, 316, 126.
*Br. J. Pharmacol.*, 1988, 93, 985.
*Eur. J. Pharmacol.*, 1987 138 303.
*Eur. J. Pharmacol.*, 1988, 149, 397.
*J. Med. Chem.* 33(1) 13–16 (1990) (Pfizer).

*Primary Examiner*—Robert Gerstl
*Attorney, Agent, or Firm*—Charles M. Caruso; Manfred Polk

[57] ABSTRACT

A class of 5-membered heterocyclic compounds having at least one heteroatom, substituted on the heterocyclic ring by an imidazolyl moiety, are useful in the treatment of psychotic disorders (e.g. schizophrenia and mania); anxiety; alcohol or drug withdrawal or dependence; pain; gastric stasis; gastric dysfunction (such as occurs with dyspepsia, peptic ulcer, reflux oesophagitis and flatulence); migraine, nausea and vomiting; movement disorders; and presenile and senile dementia.

10 Claims, No Drawings

FIVE-MEMBERED RING SYSTEMS WITH BONDED IMIDAZOLYL RING SUBSTITUENTS

This invention relates to a class of 5-membered heterocyclic compounds having at least one heteroatom, which are useful in the treatment of psychotic disorders (e.g. schizophrenia and mania); anxiety; alcohol or drug withdrawal or dependence; pain; gastric stasis; gastric dysfunction (such as occurs with dyspepsia, peptic ulcer, reflux oesophagitis and flatulence); migraine, nausea and vomiting; movement disorders; and presenile and senile dementia (also known as Alzheimer's disease and senile dementia of the Alzheimer type respectively).

The present invention provides a compound of formula I or a salt or prodrug thereof:

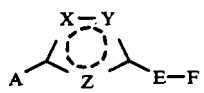
(I)

wherein the broken circle represents one or two double bonds in any position in the 5-membered ring;

X, Y and Z independently represent oxygen, sulphur, nitrogen or carbon, provided that at least one of X, Y and Z represents oxygen, sulphur or nitrogen;

A represents a group of formula II:

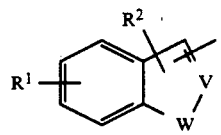
(II)

in which:

$R^1$ represents hydrogen, hydroxy, $C_{1-6}$ alkyl, $C_{2-6}$ alkenyl, $C_{2-6}$ alkynyl, $C_{1-6}$ alkoxy, hydroxy($C_{1-6}$)alkyl, halogen, amino, cyano, —$CONR^6R^7$ or —$SO_2NR^6R^7$, in which $R^6$ and $R^7$ independently represent hydrogen, $C_{1-6}$ alkyl, $C_{2-6}$ alkenyl or $C_{2-6}$ alkynyl;

$R^2$ represents hydrogen, halogen, $C_{1-6}$ alkyl, $C_{1-6}$ alkoxy or $C_{2-6}$ alkylcarbonyl;

V represents nitrogen,

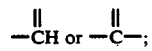

and

W represents oxygen, sulphur or —$NR^8$, in which $R^8$ represents hydrogen, $C_{1-6}$ alkyl, $C_{2-6}$ alkenyl or $C_{2-6}$ alkynyl;

E represents a bond or a straight or branched alkylene or alkenylene chain containing from 1 to 5 carbon atoms, optionally substituted with hydroxy or phenyl; and F represents an imidazolyl moiety of formula III:

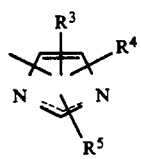
(III)

in which the broken line represents a bond in one of the two available positions; and $R^3$, $R^4$ and $R^5$ independently represent hydrogen, $C_{1-6}$ alkyl, $C_{2-6}$ alkenyl, $C_{2-6}$ alkynyl or aryl.

The ring shown as formula I may be, for example, a furan, thiophene, pyrrole, oxazole, thiazole, oxazoline, isoxazoline, thiazoline, oxadiazole, thiadiazole or imidazole ring, in particular a 1,2,4-oxadiazole, 1,3,4-oxadiazole, 1,2,4-thiadiazole or 1,3,4-thiadiazole ring. Preferably the ring is a 1,2,4-oxadiazole, 1,2,4-thiadiazole or oxazoline ring.

The group A is suitably an indole, benzofuran or benzthiophene, of formula IIA:

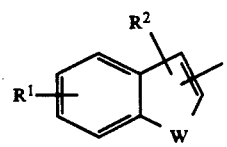
(IIA)

wherein $R^1$, $R^2$ and W are as defined above. Preferably, the group A represents an indole of structure IIB:

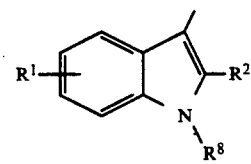
(IIB)

wherein $R^1$, $R^2$ and $R^8$ are as defined above. Preferably $R^1$ and $R^8$ independently represent hydrogen or methyl, and $R^2$ is hydrogen.

The alkylene or alkenylene chain E may be, for example, methylene, ethylene, ethenylene, 1-methylethylene, propylene, 2-methylpropylene, hydroxymethylene, 1-hydroxyethylene or phenylmethylene. When E represents an alkenylene chain, the carbon-carbon double bond(s) present therein may be in either the cis or trans configuration. Alternatively the group E may represent a single bond so that the group F is attached directly to the ring.

It will be appreciated that the point of attachment of the imidazolyl moiety F to the group E will be at any position of the imidazole ring. It will further be appreciated that the $R^3$, $R^4$ and $R^5$ substituents will occupy one each of the three remaining available positions in the imidazole ring. The imidazolyl moiety F will thus suitably be represented by part formulae IIIA-IIID as follows:

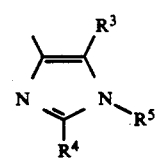
(IIIA)

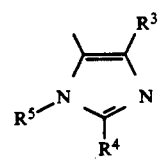
(IIIB)

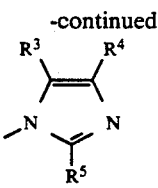

(IIIC)

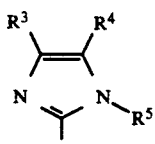

(IIID)

wherein $R^3$, $R^4$ and $R^5$ are as defined above. Preferably, the imidazolyl moiety F is a group of formula IIIA or IIIC above.

Suitably the groups $R^3$, $R^4$ and $R^5$ independently represent hydrogen or methyl. Preferably one of $R^3$, $R^4$ and $R^5$ is methyl and the other two are hydrogen; or all three simultaneously represent hydrogen.

The alkyl, alkenyl and alkynyl groups referred to with respect to any of the above formulae may represent straight, branched or cyclic groups. Thus, for example, suitable alkyl groups include methyl, ethyl, n- or iso-propyl, n-, sec-, iso- or tert-butyl, cyclopropyl, cyclobutyl, cyclopentyl or cyclohexyl, and cycloalkylalkyl groups such as cyclopropylmethyl; suitable alkenyl groups include vinyl and allyl; and suitable alkynyl groups include propargyl.

The aryl groups referred to with respect to any of the above formulae suitably include phenyl and naphthyl, optionally substituted by, for example, halogen or $C_{1-6}$ alkyl.

One sub-class of compounds within the scope of the present invention is represented by formula IVA:

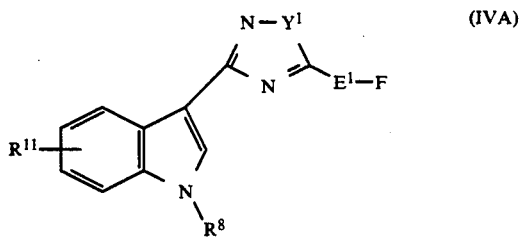

(IVA)

wherein $R^8$ and F are as defined above; $Y^1$ represents oxygen or sulphur; $E^1$ represents a group of formula —$(CH_2)_n$— or —CH=CH—, in which n is zero, 1 or 2; and $R^{11}$ represents hydrogen, halogen or $C_{1-6}$ alkyl.

A further sub-class of compounds within the scope of the present invention is represented by formula IVB:

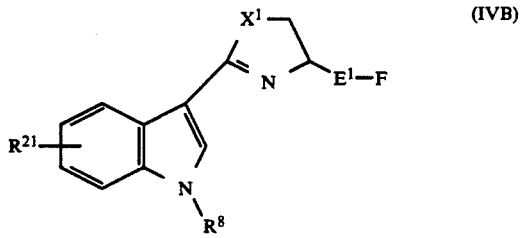

(IVB)

wherein $R^8$, $E^1$ and F are as defined above; $X^1$ represents oxygen or sulphur; and $R^{21}$ represents hydrogen, halogen or $C_{1-6}$ alkyl.

The compounds of this invention may have an asymmetric centre and some may have more than one; they can therefore exist both as enantiomers and as diastereoisomers. It is to be understood that the invention covers all such isomers and mixtures thereof.

Also included within the scope of the present invention are salts of the novel compounds. It will be appreciated that salts of the compounds for use in medicine will be non-toxic pharmaceutically acceptable salts. Other salts may, however, be useful for the preparation of the compounds of the invention or their non-toxic pharmaceutically acceptable salts. Acid addition salts, for example, may be formed by mixing a solution of the compound with a solution of a pharmaceutically acceptable non-toxic acid such as hydrochloric acid, fumaric acid, maleic acid, succinic acid, acetic acid, citric acid, tartaric acid, carbonic acid or phosphoric acid. Salts of amine groups may also comprise the quaternary ammonium salts in which the amino nitrogen atom carries an alkyl, alkenyl, alkynyl or aralkyl group. Where the novel compound carries a carboxylic acid group the invention also contemplates salts thereof, preferably non-toxic pharmaceutically acceptable salts thereof, such as the sodium, potassium and calcium salts thereof.

Specific compounds of this invention include:

5-(5-methyl-1H-imidazol-4-yl)-3-(1-methyl-1-H-indol-3-yl)-1,2,4-oxadiazole;

5-[2-(5-methyl-1H-imidazol-4-yl)ethyl]-3-(1-methyl-1H-indol-3-yl)-1,2,4-oxadiazole;

4-[(1H-imidazol-4-yl)methyl]-2-(1-methyl-1H-indol-3-yl)-(4H,5H)-oxazole;

5-[(1H-imidazol-4-yl)methyl]-3-(1-methyl-1H-indol-3-yl)-1,2,4-oxadiazole;

5-[2-(1H-imidazol-1-yl)ethyl]-3-(1-methyl-1H-indol-3-yl)-1,2,4-oxadiazole;

5-[2-(2-methyl-1H-imidazol-1-yl)ethyl]-3-(1-methyl-1H-indol-3-yl)-1,2,4-oxadiazole;

5-[2-(1H-imidazol-4-yl)ethenyl]-3-(1-methyl-1H-indol-3-yl)-1,2,4-oxadiazole;

4-[(1-methyl-1H-imidazol-4-yl)methyl]-2-(1-methyl-1H-indol-3-yl)-(4H,5H)-oxazole;

and salts and prodrugs thereof.

This invention also provides a pharmaceutical composition comprising a compound of the invention and a pharmaceutically acceptable carrier.

The compounds of the invention can be administered orally, parenterally or rectally at a daily dose of about 0.01 to 10 mg/kg of body weight, preferably about 0.1 to 1 mg/kg, and may be administered on a regimen of 1 to 4 times a day.

The pharmaceutical formulations of this invention preferably are in unit dosage forms such as tablets, pills, capsules, powders, granules, sterile parenteral solutions or suspensions, or suppositories, for oral, parenteral or rectal administration. For preparing solid compositions such as tablets, the principal active ingredient is mixed with a pharmaceutical carrier, e.g. conventional tabletting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids or mixtures of polymeric acids with such materials as shellac, cetyl alcohol and cellulose acetate.

The liquid forms in which the novel compositions of the present invention may be incorporated for administration orally or by injection include aqueous solutions, suitably flavoured syrups and flavoured emulsions with edible oils such as cottonseed oil, sesame oil, coconut oil and peanut oil, as well as elixirs and similar pharmaceutical vehicles. Suitable dispersing or suspending agents for aqueous suspension include synthetic and natural gums such as tragacanth, acacia, alginate, dextran, sodium carboxymethylcellulose, methylcellulose, polyvinylpyrrolidone and gelatin.

The oxadiazole compounds of this invention may be prepared by a process which comprises reacting a reactive derivative of a carboxylic acid of formula $R^c$—$CO_2H$ with a compound either of formula V or of formula VI, or a salt thereof:

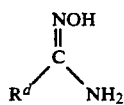 (V)

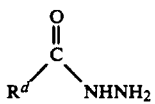 (VI)

wherein one of $R^c$ and $R^d$ is a group of formula A, and the other is a group of formula —E—F, as defined with reference to formula I above.

Suitable reactive derivatives of the acid $R^c$—$CO_2H$ include esters, for example $C_{1-4}$ alkyl esters; thioesters, for example pyridylthioesters; acid anhydrides, for example $(R^cCO)_2O$; acid halides, for example acid chlorides; orthoesters; and primary, secondary and tertiary amides.

A preferred reactive derivative of the acid $R^c$—$CO_2H$ is the iminoether derivative of formula VII:

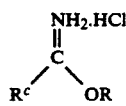 (VII)

where R is $C_{1-4}$ alkyl.

When the compound of formula V is employed the product of the reaction is a 1,2,4-oxadiazole. It will be appreciated that the compound V can also be considered as the alternative tautomeric form VA:

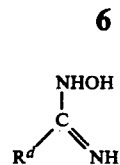 (VA)

A 3-substituted-1,2,4-oxadiazol-5-yl compound is produced if $R^c$ represents a group —E—F and $R^d$ in formula V represents a group A; whereas a 5-substituted-1,2,4-oxadiazol-3-yl compound is produced by the process of this invention when $R^c$ represents a group A and $R^d$ represents a group —E—F. A preferred reactive derivative of the acid $R^c$—$CO_2H$ in this case is a $C_{1-4}$ alkyl ester. The reaction is conveniently carried out in tetrahydrofuran, dimethylformamide or a lower alkanol such as ethanol, propanol or isopropanol at about 20° C. to 100° C. for about 1 to 6 hours.

When the compound of formula VI is employed, the product of the process of this invention is a 1,3,4-oxadiazole. In this case, a preferred reactive derivative of the acid $R^c$—$CO_2H$ is an orthoester of formula $R^cC(OR^p)_3$ where $R^p$ represents $C_{1-3}$ alkyl. The process is conveniently effected by heating the hydrazide VI with the orthoester in a solvent such as methanol at reflux temperature for about 2 to 8 hours. An intermediate of formula $R^d.CO.NH.N=C(R^c)OR^p$ may be isolated by evaporation of the solvent. The intermediate is then treated with a strong base such as potassium t-butoxide or 1,8-diazabicyclo[5.4.0]undec-7-ene, in butanol for about 10 to 24 hours at about 90° C. to 150° C.

The 1,2,4-thiadiazoles of formula I may be prepared by a process which comprises the cyclisation of a compound of formula VIII:

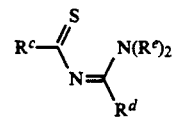 (VIII)

wherein $R^c$ and $R^d$ are as defined above, and $R^e$ is hydrogen or an alkyl group.

Cyclisation of compound VIII can be achieved using an aminating agent such as hydroxylamine-O-sulphonic acid in a lower alkanol such as methanol, ethanol or propanol, in the presence of pyridine, at between −20° C. and 50° C. for about 1-6 hours.

Cyclisation of compounds of formula VIII in which $R^e$ is hydrogen may also be achieved by use of an oxidising agent such as bromine, iodine, hydrogen peroxide or nitric acid.

The 1,2,4-thiadiazoles may also be prepared by cycloaddition of a nitrile sulphide $R^c$—C≡N+—S− with a nitrile of formula $R^dCN$ where $R^c$ and $R^d$ are as defined above.

A further method for the preparation of the 1,2,4-thiadiazoles of this invention comprises reaction of a thiadiazole of formula IX:

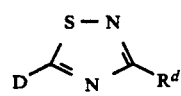 (IX)

with a reagent which provides an anion $^-R^c$, where $R^c$ and $R^d$ are as previously defined and D represents halogen. Compound IX may be prepared by the general method described in Chem. Ber., 1957, 90, 182.

Reagents which may provide the anion $-R^c$ include Grignard reagents $R^cMgHal$ (where Hal=halogen); organocuprate reagents such as $LiR^c_2Cu$; organolithium reagents $R^cLi$; or compounds which stabilise the anion by means of an adjacent activating group such as an ester or enolisable ketone function. In this case, the adjacent ester or ketone function may be retained after the process is complete, or may be removed. For example, an ester moiety may be hydrolysed and decarboxylated.

1,3,4-Thiadiazoles of this invention may be prepared by dehydration of a thiosemicarbazide of formula $R^cCSNHNHCONR^sR^t$, where $R^c$ is as defined above and $R^s$ and $R^t$ are hydrogen or an alkyl group, with a dehydrating agent such as sulphuric acid, polyphosphoric acid or methanesulphonic acid; followed by attachment of the $R^d$ group by conventional means.

The oxadiazoles and thiadiazoles of this invention wherein E represents an ethylene group, optionally substituted by one or more phenyl groups, and F represents an imidazolyl moiety of formula IIIC above may additionally be prepared by reacting a compound of formula X with an imidazole derivative of formula XI:

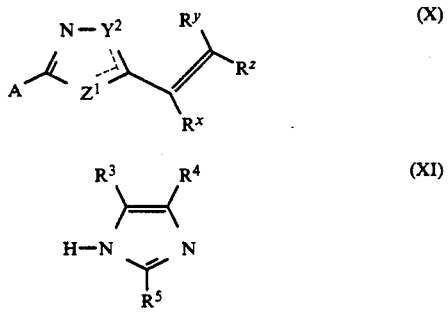

wherein the broken line represents a bond in one of the two available positions; A, $R^3$, $R^4$ and $R^5$ are as defined above; one of $Y^2$ and $Z^1$ represents nitrogen and the other represents oxygen or sulphur; and $R^x$, $R^y$ and $R^z$ independently represents hydrogen or phenyl. The reaction is conveniently carried out at room temperature in a suitable solvent, e.g. an alcohol such as methanol.

The oxazoles and thiazoles of this invention may be prepared by reaction of an amide or thioamide of formula XII with a α-haloketone of formula XIII:

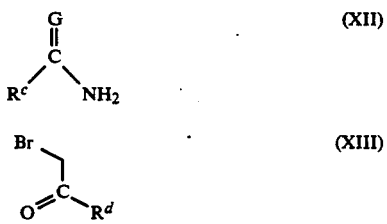

wherein G is oxygen or sulphur, and $R^c$ and $R^d$ are as defined above. The conditions for this reaction are as described in *Synthesis*, 1975, 389.

The imidazoles of this invention may be prepared by conventional methods, such as are described in *Advances in Heterocyclic Chemistry*, 1970, 12, 104. One suitable process may be illustrated as follows:

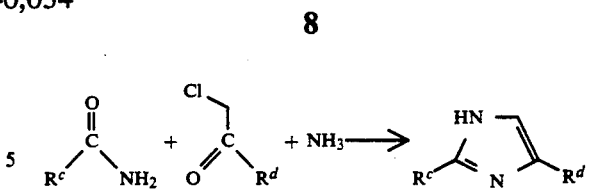

As will be appreciated, this method may also be adapted to the preparation of the imidazolyl moiety F, which may be introduced into the compounds according to the invention at an appropriate stage in the synthetic sequence.

The oxazoline and thiazoline compounds of this invention may b prepared by a process which comprises reacting a reactive derivative of a carboxylic acid of formula $R^c$—$CO_2H$ with a compound either of formula XIV or of formula XV, or a salt thereof;

wherein G is oxygen or sulphur and $R^c$ and $R^d$ are as defined above.

The process is conveniently effected by condensation of the starting materials in the presence of thionyl chloride, phosphorus oxychloride or triphenylphosphine/diethyl azodicarboxylate.

The intermediate of formula XV may be prepared by conventional methods, for example:

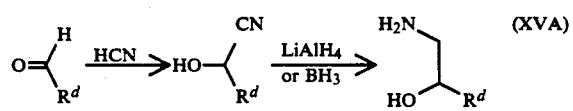

The isoxazoline compounds of this invention may be prepared by reacting a nitrile oxide with an appropriate alkene.

The furans according to the invention may, for example, be prepared by reacting a compound of formula XVI:

with a reagent which provides an anion $-R^c$, wherein $R^c$ and $R^d$ are as previously defined; and wherein the reagent which may provide the anion $-R^c$ is suitably as described with reference to formula IX above.

The intermediate of formula XVI may be prepared by conventional methods, for example:

-continued

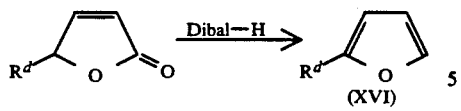

After any of the above described processes is complete, one substituent can be converted to another. For example an amino group may be converted to chloro, or hydrazo, —NHNH$_2$, via the intermediacy of diazonium, —N$_2$. Similarly, a chloro substituent may be converted to methoxy by reaction with a nucleophile such as methoxide; alkoxycarbonyl groups may be converted, via carboxy, to an amino substituent, —NH$_2$; and methoxy may be converted to hydroxy by treatment with concentrated hydrobromic acid.

In any of the above reactions it may be necessary and/or desirable to protect any sensitive groups in the compounds. For example, if R$^c$ and/or R$^d$ include amino, carboxy, keto, hydroxy or thiol groups, these may be protected in conventional manner. Thus, suitable protecting groups for hydroxy groups include silyl groups such as trimethylsilyl or t-butyldimethylsilyl, and etherifying groups such as tetrahydropyranyl; and for amino groups include benzyloxycarbonyl and t-butoxycarbonyl. Keto groups may be protected in the form of a ketal. Carboxy groups are preferably protected in a reduced form such as in the form of their corresponding protected alcohols, which may be subsequently oxidised to give the desired carboxy group. Thiol groups may be protected by disulphide formation, either with the thiol itself or with another thiol to form a mixed disulphide. The protecting groups may be removed at any convenient stage in the synthesis of the desired compound according to conventional techniques.

The following Examples illustrate the preparation of compounds according to the invention.

The compounds according to the present invention may be evaluated for their anti-emetic activity in the von Bezold-Jarisch test (Nature, 1985, 316, 126), or in animal models of anxiety (see, for example, Br. J. Pharmacol., 1988, 93, 985), schizophrenia (see, for example, Eur. J. Pharmacol., 1987, 138, 303) or cognition (passive avoidance assay).

Certain of the compounds of the present invention act on 5-HT$_3$ receptors and this may account, in whole or in part, for the pharmacological activity of these compounds. The 5-HT$_3$ binding of the compounds of the invention was assayed using the protocol described in the literature (Eur. J. Pharmacol., 1988, 149, 397); the $^3$[H] methylated quaternary derivative of formula XVII was employed as a radioligand:

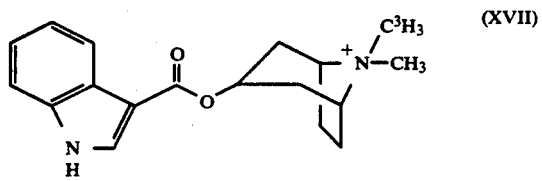

The compounds of each of the Examples demonstrate an affinity for the 5-HT$_3$ receptor with a K$_i$ (dissociation constant for the displacement of radioligand) better than 100 nM.

EXAMPLE 1

5-(5-Methyl-1H-imidazol-4-yl)-3-(1-methyl-1H-indol-3-yl)-1,2,4-oxadiazole hydrochloride a) (1-Methyl-1H-indol-3-yl)amino oxime A solution of hydroxylamine hydrochloride (1.3 g), ptassium carbonate (3.5 g) and 1-methyl-1H-indole-3-nitrile (2 g) in absolute ethanol (100 ml) was heated at reflux for eight hours. The solvent was removed at reduced pressure and the residue extracted with ether (2×100 ml). The solvent was evaporated at reduced pressure and the residue was purified by recrystallisation from dichloromethane/acetone to afford the title compound as a white solid (2.9 g), m.p. 110° C. (dec); Found: C, 63.50; H, 5.94; N, 22.27; C$_{10}$H$_{11}$N$_3$O requires C, 63.48; H, 5.86; N, 22.21%; $\delta_H$(360 MHz, CDCl$_3$), 3.6 (3H, s, NCH$_3$), 6.8–7.0 (2H, m, H-5, H-6), 7.11 (1H, d, J,=8.0 Hz, H-7), 7.20 (1H, s, H-2), 7.90 (1H, d, J=8.0 Hz, H-4); m/z 173 (25%), 158 (40), 156 (100).

b) Ethyl 5-methyl-1-triphenylmethyl-4-1H-imidazolecarboxylate

Ethyl 5-methyl-4-1H-imidazolecarboxylate (6.16 g) in toluene (100 ml), triphenylmethyl chloride (11.12 g) and triethylamine (5.6 ml) were heated at reflux for 18 h. Toluene was removed under reduced pressure and the residue was dissolved in dichloromethane (100 ml), washed with water (4×50 ml) dried (MgSO$_4$) and evaporated. The residue was purified by column chromatography on silica using 1% methanol in dichloromethane as eluant with a trace of triethylamine. This afforded the title compound (11 g), m.p. 188°–190° C. $\delta_H$(250 MHz, CDCl$_3$) 1.38–1.42 (3 H, t, J=6.5 Hz, CH$_3$), 1.86 (3 H, s, CH$_3$), 4.36–4.40 (2 H, q, J=7.2 Hz, CH$_2$), 7.10–7.46 (16 H, m, ArH); m/z (NoM+), 243 (Ph$_3$C+, 100%).

c) 3-(1-Methyl-1H-indol-3-yl)-5-(5-methyl-1-triphenylmethyl-1H-imidazol-4-yl)-1,2,4-oxadiazole A solution of (1-methyl-1H-indol-3-yl)amide oxime (0.57 g) in tetrahydrofuran (30 ml) was stirred over 4A molecular sieves for 30 minutes. Sodium hydride (50% dispersion in oil, 0.14 g) was added and the suspension was heated at 50° C. for 30 minutes. The mixture was cooled to room temperature and ethyl 5-methyl-1-triphenylmethyl-4-1H-imidazolecarboxylate (2.0 g) was added. The mixture was heated at reflux for 4 h under nitrogen, cooled, filtered and evaporated. The residue was purified by column chromatography on silica using dichloromethane as eluant with gradient elution to 5% ethyl acetate in dichloromethane. This afforded the title compound (1.1 g). $\delta_H$ (250 MHz, CDCl$_3$) 2.00 (3H, s, CH$_3$), 3.80 (3H, s, N—CH$_3$), 7.17–7.39 (17H, m, ArH), 7.52 (1H, s, C-H), 7.91 (1H, s, C—H), 8.27 (1H, dd, J=6.3, 2.5 Hz, ArH).

d) 5-(5-Methyl-1H-imidazol-4-yl)-3-(1-methyl-1H-indol-3-yl)-1,2,4-oxadiazole hydrochloride 3-(1-Methyl-1H-indol-3-yl)-5-(5-methyl-1-triphenylmethyl-1H-imidazol-4-yl)-1,2,4-oxadiazole (1.1 g) was suspended in methanolic hydrogen chloride. The mixture was stirred for 30 minutes and was refrigerated for 6 h. The title compound was filtered yielding (0.5 g) as a white powder, m.p. 260°–262° C. Found: C, 57,02; H, 4.58; N, 22.07; C$_{15}$H$_{13}$N$_5$O.HCl requires C, 57.06; H, 4.47; N, 22.19%; $\delta_H$(360 MHz, DMSO-d$_6$) 2.70 (3H, s, CH$_3$), 3.92 (3H, s, N-CH$_3$), 7.27 (1H, t, J=6.2 Hz, CH), 7.32 (1H, t, J=6.1 Hz, CH), 7.59 (1H, d, J=7.5 Hz, CH), 8.10 (1H, d, J=7.5 Hz, CH), 8.17 (1H, s, CH), 8.68 (1H, s, CH); m/z 279 (M+, 70%).

EXAMPLE 2

5-[5-Methyl-1H-imidazol-4-yl)ethyl]-3-(1-methyl-1H-indol-3-yl)-1,2,4-oxadiazole hydrogen oxalate a) Dimethyl [(5-methyl-1H-imidazol-4-yl)methyl] malonate Sodium (4.0 g) was dissolved in methanol (300 ml) at reflux followed by dropwise addition of dimethylmalonate (20.0 ml). The solution was cooled to −5° C. and 5-bromomethyl-4-methyl-1H-imidazole hydrogen bromide salt (14.9 g) was added. The temperature was maintained for 1.5 hours, then allowed to warm to room temperature overnight. The solvent was evaporated at reduced pressure and the residue purified by silica gel chromatography eluting with dichloromethane/methanol (95.5) to afford the title compound as a yellow waxy solid (5.8 g). $\delta_H$ (360 MHz, CDCl$_3$), 2.19 (3H, s, CH$_3$), 3.11 (2H, d, J=7.1 Hz, CH$_2$), 3.72 (6H, s, 2×OCH$_3$), 3.79 (1H, t, J=7.1 Hz, C-H), 7.43 (1H, s, H-2).

b) Methyl 4-methyl-5-1H-imidazolepropionate

A solution of the aforementioned diester (3.5 g), dimethylsulphoxide (40 ml) and water (1 ml) was heated at reflux for 4 hours. Water (70 ml) was added and the solution extracted with dichloromethane (4×50 ml), the combined organic extracts dried (Na$_2$SO$_4$) and concentrated to dryness. The residual oil was purified by silica gel chromatography eluting with dichloromethane/methanol (95:5) to yield a yellow crystalline solid (1.55 g). A small sample (100 mg) was further purified by the formation of the oxalate salt in ethereal solution to afford the title compound as a white crystalline solid (140 mg), m.p. 135° C. Found: C, 46.48; H, 5.47; N, 10.83; C$_8$H$_{12}$N$_2$O$_2$.(COOH)$_2$ requires C, 46.51; H, 5.46; N, 10.85%; $\delta_H$ (360 MHz, D$_2$O), 2.26 (3H, s, CH$_3$), 2.72 (2H, t, J=7.1 Hz, CH$_2$), 2.97 (2H, t, J=7.1 Hz, CH$_2$CO), 3.67 (3H, s, OCH$_3$), 8.42 (1H, s, H-2);m/z 169 ((M+1)+, 100%, CI+).

c) 5-[(5-Methyl-1H-imidazol-4-yl)ethyl]-3-(1-methyl-1H-indol-3-yl)-1,2,4-oxadiazole hydrogen oxalate A solution of (1-methyl-1H-indol-3-yl) amide oxime (0.71 g) in tetrahydrofuran (30 ml) was stirred over molecular sieves (0.08 g, 4A) for 1 hour. Sodium hydride (55% dispersion in oil, 0.13 g) was added and the solution stirred for 20 minutes before the addition of methyl 4-methyl-5-1H-imidazolepropionate free base (0.35 g). The mixture was heated at reflux for 3 hours, cooled, filtered and evaporated to dryness. The residual oil was dissolved in dichloromethane (35 ml) and washed successively with water (20 ml) and saturated brine solution (20 ml), dried (Na$_2$SO$_4$) and concentrated. The resulting oil was purified by flash silica gel chromatography eluting with dichloromethane/methanol (95:5) to yield a buff-coloured soiid (0.26 g). This was further purified by formation of the oxalate salt in ethereal solution to afford the title compound as a white crystalline solid (0.25 g); m.p. 192°-194° C. (dec). Found: C, 57.12; H, 4.97; N, 17.32; C$_{17}$H$_{17}$N$_5$O.(COOH)$_2$ requires C, 57.43; H, 4.82; N, 17.62%; $\delta_H$(360 MHz, DMSO-d$_6$), 2.17 (3H, s, CH$_3$), 3.11 (2H, t, J=7.3 Hz, CH$_2$), 3.28 (2H, t, J=7.3 Hz, CH$_2$), 3.89 (3H, s, NCH$_3$), 7.21-7.32 (2H, m, ArH), 7.56 (1H, d, J=8.2 Hz, H-7), 8.01 (1H, d, J=7.7 Hz, H-4), 8.09 (1H, s, H-2), 8.45 (1H, s, C-H); m/z 307 (M$^{30}$, 20%), 171 (70) 95 (100).

EXAMPLE 3

(4S)-4-[(1H-Imidazol-4-yl)methyl]-2-(1-methyl-1H-indol-3-yl)-(4H, 5H)-oxazole hydrochloride hemihydrate a) Methyl (1-methyl-1H-indol-3-yl)imidate hydrochloride Dry hydrogen chloride gas was bubbled through a solution of 1-methyl-1H-indole-3-nitrile (1.7 g) in dry methanol (30 mls). After standing at room temperature for 24 h addition of dry ether gave the title compound as colourless needles (1.8 g), m.p. 156°-8° C. (dec). Found: C, 58.87; H, 5.91; N, 12.53; Cl, 15.72. Calcd. for C$_{11}$H$_{12}$N$_2$O.HCl: C, 58.80; H, 5.83; N, 12.47; Cl, 15.78%; $\delta_H$ (360 MHz, DMSO-d$_6$), 3.9 (3H, s, NCH$_3$), 4.3 (3H, s, OCH$_3$), 7.3 (1H, dt, J=7.4 and 1.2 Hz, CH), 7.4 (1H, dt, J=8.2 and 1.6 Hz, CH), 7.7 (1H, d, J=7.8 Hz, CH), 7.9 (1H, dd, J=6.7 and 1.1 Hz, CH), 9.0 (1H, s, CH); m/z 188 (M+).

4b) (4S)-4-[(1H-Imidazol-4-yl)methyl]-2-(1-methyl-1H-indol-3-yl)-(4H, 5H)-oxazole hydrochloride hemihydrate L-Histidinol dihydrochloride (1.0 g) was stirred under nitrogen with triethylamine (1.3 ml) in methanol (20 mls) for 30 mins to give a clear solution. The methyl (1-methyl-1H-indol-3-yl) imidate hydrochloride (1.0 g), dissolved in methanol, was added and after stirring for 24 hours the solution was heated under reflux for 24 hours. After evaporation to dryness the residue was partitioned between dilute ammonium hydroxide solution and dichloromethane. The organic phase was separated and the aqueous phase extracted with dichloromethane (3×50 ml). The organic phase and extracts were combined, dried (MgSO$_4$) and solvents evaporated in vacuo. After purification by chromatography on silica eluting with dichloromethane/methanol/.880 ammonium hydroxide (90:10:1) the title compound was crystallised from dichloromethane as colourless crystals. A portion of the base was dissolved in dichloromethane and treated with ethereal hydrogen chloride to give the title compound 0.14 g, m.p. 251°-252° C. [α]$_D^{20}$ −8.8 (c×1, MeOH). Found: C, 58.71; H, 5.67; N, 17.13; Cl, 11.14; C$_{16}$H$_{16}$N$_4$O.HCl.0.5H$_2$O requires C, 58.99; H, 5.57; N, 17.20; Cl, 10.88%. $\delta_H$ (360 MHz, D$_2$O) 3.14 (1H, dd, J=16.7, 5.0 Hz, CHH), 3.52 (1H, dd, J=16.7, 8.0 Hz, CHH), 3.84 (3H, s, NCH$_3$), 4.35 (1H, dd, J=12.4, 5.0 Hz, CHHO) 4.69–4.75 (1H, m, CHHO), 5.26–5.36 (1H, m, CHN), 7.23 (1H, s, CHN), 7.33 (1H, t, J=7.1 Hz, CH), 7.39 (1H, t, J,=7.1 Hz, CH), 7.55 (1H, d, J=8.4 Hz, CH), 7.82 (1H, s, CH), 8.01 (1H, d, J=7.4 Hz, CH), 8.62 (1H, s, NCHN), m/z 280 (M+ free base).

EXAMPLE 4

5-[(1H-Imidazol-4-yl)methyl]-3-(1-methyl-1H-indol-3-yl)-1,2,4-oxadiazole hydrochloride a) Methyl (1H-imidazol-4-yl)acetate hydrochloride 1H-Imidazole-4-acetic acid (5 g) was dissolved in methanolic hydrogen chloride (150 ml) and stirred at room temperature for 72 hours. Evaporation to dryness gave the title compound as a white solid, m.p. (5.3 g). $\delta_H$ (360 MHz, D$_2$O) 3.77 (3H, s, O-CH$_3$), 3.95 (2H, s, CH$_2$), 7.39 (1H, s, CH), 8.66 (1H, s, CH).

b) methyl (1-triphenylmethyl-1H-imidazol-4-yl)acetate

Triethylamine (4.2 ml) was added to a suspension of methyl (1H-imidazol-4-yl) acetate hydrochloride (5.3 g) in dry toluene (150 ml). This was stirred for 1 h; triphenylmethyl chloride (8.34 g) and triethylamine (4.2 ml) were added to the mixture which was heated at reflux for 8 h. The mixture was cooled and evaporated to dryness. The residue was dissolved in dichloromethane and washed with water (4×100 ml), dried (MgSO$_4$) and the solvent was removed under reduced pressure. The residue was purified by column chromatography on silica, using 5% methanol in dichloromethane as eluant, to afford the title compound, (7.2 g), m.p. 122°–125° C.; $\delta_H$ (360 MHz, CDCl$_3$) 3.62 (2H, s, CH$_2$), 3.69 (3H, s, OCH$_3$), 6.77 (1H, s, CH), 7.11–7.16 (6H, m, CH), 7.30–7.37 (10H, m, CH); m/z 243 (Ph$_3$C+, 100%), no M$^{30}$.

c) 3(1-Methyl-1H-indol-3-yl)-5-[(1-triphenyl-methyl-1H-imidazol-4-yl)methyl]-1,2,4-oxadiazole (1-Methyl-1H-indol-3-yl)amine oxime (0.8 g) in dry tetrahydrofuran (30 ml) was stirred over 4A molecular sieves for 30 min; sodium hydride (50% dispersion in oil, 0.12 g) was added to the mixture which was heated at reflux for 30 min, and then cooled to room temperature. Methyl (1-triphenylmethyl-1H-imidazol-4-yl) acetate (2.67 g) was added. the mixture was heated at reflux for 2 h, cooled and filtered to remove molecular sieves. The solvent was removed under reduced pressure and the residue was purified by column chromatography on silica using 5% methanol in dichloromethane as eluant. The title compound was recrystallised from methanol/dichloromethane, (1.25 g). $\delta_H$ (360 MHz, CDCl$_3$) 3.89 (3H, s, N-CH$_3$), 4.32 (2H, s, CH$_2$), 6.95 (1H, s, CH), 7.18–7.21 (7H, m, CH), 7.30–7.41 (11H, m, CH), 7.47 (1H, d, J=1.3 Hz, CH), 7.79 (1H, s, CH), 8.23–8.26 (1H, dd, J=7.0, 1.0 Hz, CH); m/z 521 (M+, 5%), 243 (Ph$_3$C+, 100%).

d) 5-[(1H-Imidazol-4-yl)methyl]-3-(1-methyl-1H-indol-3-yl)-1,2,4-oxadiazole hydrochloride 3-(1-Methyl-1H-indol-3-yl)-5-[(1-triphenylmethyl-1H-imidazol-4-yl)methyl]-1,2,4-oxadiazole (1.25 g) was dissolved in methanolic hydrogen chloride solution (50 ml) and stirred at room temperature for 48 h. The title compound precipitated from solution as a white solid (0.92 g), m.p. 255°–257° C. Found: C, 56.95; H, 4.56; N, 21.99; Cl, 11.17; C$_{15}$H$_{13}$N$_5$O.HCl requires C, 57.05; H, 4.47; N, 22.17; Cl, 11.22%; $\delta_H$ (360 MHz, DMSO-d$_6$) 3.88 (3H, s, CH$_3$), 4.61 (2H, s, CH$_2$), 7.24 (1H, t, J=6.9 Hz, CH), 7.30 (1H, t, J=6.9 Hz, CH), 7.57 (1H, d, J=8.1 Hz, CH), 7.70 (1H, s, CH), 8.02 (1H, d, J,=7.4 Hz, CH), 8.10 (1H, s, CH), 9.10 (1H, s, CH); m/z 279 (M+, free base, 100%).

EXAMPLE 5

5-[2-(1H-Imidazolyl)ethyl]-3-(1-methyl-1H-indol-3-yl)-1,2,4-oxadiazole hydrochloride a) 2-[3-(1-Methyl-1H-indol-3-yl)-1,2,4-oxadiazol-5-yl]ethene

[1-Methyl-1H-indol-3-yl]amide oxime (1.89 g) and powdered molecular sieves (2 g, 4A) were suspended in anhydrous THF (40 ml) under a nitrogen atmosphere and were stirred for 30 min. NaH (0.52 g, 50% dispersion in oil) was added and the mixture was heated at 60° C. for 15 min. The mixture was cooled to room temperature and methyl acrylate (0.9 ml) added. This was stirred for 15 min at room temperature and then heated at reflux for 1 hour. The reaction was quenched with water and the solvent was removed under reduced pressure. The residue was partitioned between CH$_2$Cl$_2$ and water. The organic layer was separated, dried (Na$_2$SO$_4$) and the solvent evaporated at reduced pressure. The residue was purified by chromatography on silica using CH$_2$Cl$_2$ as eluant. This afforded a colourless oil which solidified upon refrigeration to a white crystalline material, 0.5 g, m.p. 54°–55° C. (ether/hexane). Found: C, 69.32; H, 5.04; N, 18.63; C$_{13}$H$_{11}$N$_3$O requires C, 69.32; H, 4.92; N, 18.65%; $\delta_H$ (360 MHz, CDCl$_3$)3.79 (3H, s, NCH$_3$), 5.92 (1H, dd, J=11.0, 0.7 Hz, CH=CH$_2$), 6.54 (1H, dd, J=18.0, 0.7 Hz, CH=CH$_2$), 6.74 (1H, dd, J=18.0, 11.0 Hz, CH=CH$_2$), 7.26–7.34 (3H, m, H-5, H-7, ArH), 7.76 (1H, s, ArH, H-2), 8.23–8.26 (1H, m, ArH, H-4); m/z 225 (M+, 100%), 172 (40), 156 (40).

b) 5-[2-(1H-(Imidazolyl)ethyl]-3-(1-methyl-1H-indol-3-yl)-1,2,4-oxadiazole hydrochloride 2-[3-(1-Methyl-1H-indol-3-yl)-1,2,4-oxadiazol-5-yl]ethene (1.1 g) and 1H-imidazole (1.34 g) were suspended in methanol (30 ml) and were refluxed overnight. Methanol was removed under reduced pressure and the residue was suspended in dichloromethane and washed with water (3×100 ml). The organic layer was dried (MgSO$_4$) and evaporated to yield a pale yellow solid. This was purified by chromatography on silica using 5% methanol in chloroform as eluant. The resulting pale yellow crystalline material was treated with methanolic hydrogen chloride affording the crystalline salt, 1.8 g, m.p. 182°–184° C. (methanol). Found: C, 58.35; H, 5.00; N, 21.48; Cl, 10.71. C$_{16}$H$_{15}$N$_5$O.HCl requires C, 58.27; H, 4.89; N, 21.24; Cl, 10.75%; $\delta_H$ (360 MHz, D$_2$O), 3.45 (2H, t, J=6.7 Hz, —CH$_2$CH$_2$N), 3.63 (3H, s, CH$_3$), 4.70 (2H, t, J=6.7 Hz, —CH$_2$CH$_2$N), 7.18–7.26 (2H, m, H-5, H-6), 7.26–7.30 (2H, m, H-7, C-H), 7.39 (1H, s, H-2), 7.57 (1H, m, C-H), 7.61(1H, m, H-4), 7.65 (1H, m, C-H), 8.86 (1H, s, C-H); m/z 293 (M+, free base, 90%), 225 (90), 171 (100).

EXAMPLE 6

5-[2-(2-Methyl-1H-imidazolyl)ethyl]-3-(1-methyl-1H-indol-3-yl)-1,2,4-oxadiazole hydrochloride hydrate 2-[3-(1-Methyl-1H-indol-3-yl)-1,2,4-oxadiazol-5-yl]ethene was prepared as described in Example 5. This alkene (0.25 g) was dissolved in methanol (20 ml) and dichloromethane (10 ml). 2-Methyl-1H-imidazole (0.85 g), excess, was added and the solution was heated at reflux for 12 h. The solvents were removed under reduced pressure and the residue was purified by chromatography on silica using 6% methanol in chloroform as eluant. This furnished the product as a yellow powder. This was recrystallised from dichloromethane yielding a yellow microcrystalline substance, (0.19 g). It was further purified by treatment with methanolic hydrogen chloride to yield the monohydrochloride, m.p. 182° C. (dec). Found: C, 56.93; H, 5.51; N, 19.54; Cl, 9.92. C$_{17}$H$_{17}$N$_5$O. HCl.H$_2$O requires C, 56.43; H, 5.57; N, 19.36; Cl, 9.80%; $\delta_H$(360 MHz; D$_2$O), 2.64 (3H, s, CH$_3$), 3.37 (2H, t, J=6.6 Hz, CH$_2$), 3.62 (3H, s, CH$_{3indole}$), 4.50 (2H, t, J=6.6 Hz, CH$_2$), 7.18–7.31 (3H, m, ArH$_{indole}$, H-5, H-6, H-7), 7.33 (1H, s, ArH$_{indole}$, H-2), 7.38 (1H, d, J=2.1Hz, ArH$_{imidazole}$), 7.44 (1H, d, J=2.1 Hz, ArH$_{imidazole}$), 7.59 (1H, d, J=7.8 Hz, ArH$_{indole}$, H-4); m/z 307 (M+, free base, 90%), 225 (100), 171 (70).

EXAMPLE 7

(4R)-4-(1H-Imidazol-4-yl-methyl)-2-(1-methyl-1H-indol-3-yl)-(4H, 5H)-oxazole hydrochloride a) Methyl 2-amino-3-(1H-imidazol-4-yl)propanoate D-Histidine hydrochloride monohydrate (5 g) was suspended in methanolic hydrogen chloride (75 mls)

and stirred at room temperature for 96 hours. It was heated at reflux for 12 hours and evaporated to dryness. The residue was recrystallised from methanol/ethyl acetate to afford the title compound (3.5 g), m.p. 196°-198° C. $\delta_H$ (250 MHz, D$_2$O) 3.38-3.55 (2H, m, CH$_2$), 3.85 (3H, s, OCH$_3$), 4.51 (1H, t, J=6.8 Hz, CH), 7.45 (1H, s, CH), 8.71 (1H, d, J=1.4 Hz, CH). m/z=169 (10%).

b) 2-Amino-3-(1H-imidazol-4-yl)propanol dihydrochloride

Methyl 2-amino-3-(1H-imidazol-4-yl)propanoate (3.5 g) was suspended in tetrahydrofuran (50 mls) under nitrogen and cooled to −40° C. Lithium aluminium hydride (1.0M in tetrahydrofuran, 43.5 mls) was added slowly. The mixture was allowed to return to room temperature and stirred for 1 hour, then heated under reflux for 3 hours. The reaction mixture was allowed to cool and quenched with tetrahydrofuran/water 9:1 (15 mls). The mixture was evaporated to dryness and the residue placed in a Soxhlet extractor with tetrahydrofuran (300 mls) and extracted continuously for 15 hours. The extract was evaporated to give the title compound (1.1 g). $\delta_H$(250 MHz, MeOD), 2.58 (1H, dd, J=17.5 7.5 Hz), 2.74 (1H, dd, J=17.5, 7.5 Hz, CH$_2$), 3.00-3.10 (1H, m, CH), 3.32-3.42 (1H, m, CHH), 3.52-3.62 (1H, m, CHH), 6.86 (1H, s, CH) abd 7.62 (1H, s, CH).

c) (4R)-4-(1H-Imidazol-4-yl-methyl)-2-(1-methyl-1H-indol-3-yl)-(4H, 5H)-oxazole hydrochloride This was prepared following the method of Example 3; 2-amino-3-(1H-imidazol-4-yl)propanol dihydrochloride (1.1 g) was reacted with methyl (1-methyl-1H-indol-3-yl)imidate hydrochloride (1.6 g) to afford the free base (0.75 g). A portion of the free base was treated with methanolic hydrogen chloride and recrystallised from ethanol to give the title compound, m.p. 252°-254° C.; $\alpha_D$ [c=1, MeOH]=9.6?. Found: C, 60.65; H, 5.46; N, 17.59; Cl, 11.22; C$_{16}$H$_{16}$N$_4$O.HCl requires C, 60.66; H, 5.41; N, 17.68; Cl, 11.19%; $\delta_H$ (360 MHz, D$_2$O) 3.13 (1H, dd, J=16.6, 5.1 Hz), 3.52 (1H, dd, J=16.6, 7.9 Hz, CH$_2$), 3.83 (3H, s, CH$_3$), 4.34 (1H, dd, J=12.4, 5.0 Hz, CHH), 4.7 (1H, m, CHH), 5.26-5.32 (1H, m, CH), 7.23 (1H, s, CH), 7.33 (1H, t, J=7.1 Hz, CH), 7.39 (1H, t, J=7.1 Hz, CH), 7.54 (1H, d, J=8.2 Hz, CH), 7.81 (1H, s, CH), 8.01 (1H, d, J=7.8 Hz, CH), 8.62 (1H, s, CH); m/z=280 (10), 158 (100).

EXAMPLE 8

5-[(1H-Imidazol-4-yl)-ethenyl]-3-(1-methyl-1H-indol-3-yl)-1,2,4-oxadiazole hydrochloride a) Methyl 3-(1H-imidazol-4-yl)acrylate 3-(1H-Imidazol-4-yl)acrylic acid (5 g) was suspended in methanolic hydrogen chloride (100 mls) and heated at reflux for 24 hours. After cooling, the product was filtered and the crystalline solid was washed with diethyl ether (5.36 g), m.p. 234°-236° C. (dec). $\delta_H$ (360 MHz, D$_2$O) 3.85 (3H, s, CH$_3$), 6.57 (1H, d, J=16.3 Hz, CH), 7.60 (1H, d, J=16.3 Hz, CH), 7.83 (1H, s, CH), 8.86 (1H, s, CH); m/z 152 (70%).

b) 5-(1H-Imidazol-4-yl)ethenyl]-3-(1-methyl-1H-indol-3-yl)-1,2,4-oxadiazole hydrochloride (1-Methyl-1H-indol-3-yl)amide oxime (1.89 g) was dissolved in tetrahydrofuran (40 mls) and stirred with 4A molecular sieves, under nitrogen. Sodium hydride (60% dispersion in oil, 1.2 g) was added slowly and the mixture was heated for 30 minutes. Methyl 3-(1H-imidazol-4-yl) acrylate (1.53 g) was added and the mixture was refluxed for a further 2 hours, then allowed to cool. The residue was dissolved in dichloromethane, filtered and evaporated to dryness. The residue was purified by column chromatography on silica, eluting with dichloromethane/methanol/.880 ammonia 93:7:1. The residue was recrystallised from ethyl acetate, then dissolved in methanol and treated with ethereal hydrogen chloride to give the title compound as a precipitate (200 mg), m.p. 250° C. Found: C, 58.43; H, 4.43; N, 21.08; Cl, 11.28; C$_{16}$H$_{13}$N$_5$O. HCl requires C, 58.63; H, 4.31; N, 21.37; Cl, 10.84%; $\delta_H$ (360 MHz, DMSO-d$_6$) 3.84 (3H, s, CH$_3$), 7.18 (1H, t, J=7.0 Hz, CH), 7.25 (1H, d, J=7.0 Hz, CH), 7.43 (1H, d,J=16.5 Hz, CH), 7.51 (1H, d, J=8.0 Hz, CH), 7.75 (1H, d, J=16.4 Hz, CH), 8.00 (1H, d, J=7.2 Hz, CH), 8.02 (1H, s, CH), 8.08 (1H, s, CH); 9.06 (1H, s, CH); m/z 291 (M+, 30%).

EXAMPLE 9

(4S)-4-[(1-Methyl-1H-imidazol-4-yl)methyl]-2-(1-methyl-1H-indol-3-yl)-(4H, 5H-oxazole oxalate dihydrate (4S)-4-[(1H-Imidazol-4-yl)methyl]-2-(1-methyl-1H-indol-3-yl)-(4H, 5H)-oxazole (0.5 g) was added to a suspension of sodium amide in liquid ammonia (50 ml). Sodium amide was prepared in situ from sodium (0.06 g) and a crystal of ferric chloride. This black suspension was stirred for 30 min. Methyl iodide (0.25 ml) was added and the mixture was stirred for 2 h. THF (20 ml) was added and the ammonia was allowed to evaporate overnight. The residue was partitioned between water and dichloromethane. The aqueous layer was extracted (3×100 ml) and the extracts combined, dried over MgSO$_4$ (anhydrous) and evaporated. The residue was purified by column chromatography on silica using 5% methanol in dichloromethane, yielding the product (0.12 g). This was treated with ethereal oxalic acid and the oxalate salt was recrystallized from ethyl acetate/methanol affording white needles, m.p. 174°-175° C. Found: C, 54.54; H, 5.43; N, 13.38. C$_{17}$H$_{18}$N$_4$O.C$_2$D$_4$H$_2$.2H$_2$O requires C, 54.28; H, 5.75; N, 13.32%. $\delta_H$ (360 MHz, D$_2$O) 3.11 (3H, s, NCH$_3$), 3.27 (1H, dd, J =17.2, 4.7 Hz, H$_A$CH$_2$), 3.43 (1H, dd, J=25.8, 17.2 Hz, H$_B$CH$_2$), 3.86 (3H, s, CH$_3$), 4.52 (1H, dd, J=12.6, 5.1 Hz, H$_A$ ring CH$_2$), (H$_B$ buried under D$_2$O suppression peak), 5.75 (1H, m, CH), 7.20 (1H, s, CH im), 7.30 (1H, t, J=7.2 Hz, CH), 7.38 (1H, t, J=7.2 Hz, CH), 7.56 (1H, d, J=8.2 Hz, CH), 7.69 (1H, s, H-2), 7.77 (1H, d, J=7.9 Hz, CH), 8.64 (1H, s, CH im); m/z (CI$^{30}$) 295 (M$^{30}$ +1, free base, 100%).

EXAMPLE 10

Tablet Preparation

Tablets containing 1.0, 2.0, 25.0, 26.0, 50.0 and 100.0 mg, respectively of:

5-[5-Methyl-1H-imidazol-4-yl)ethyl]-3-(1-methyl-1H-indol-3-yl)-1,2,4-oxadiazole hydrogen oxalate (4S)-4-[(1H-Imidazol-4-yl)methyl]-2-(1-methyl-1H-indol-3-yl)-(4H, 5H)-oxazole hydrochloride hemihydrate (4R)-4-(1H-Imidazol-4-yl-methyl)-2-(1-methyl-1H-indol-3-yl)-(4H, 5H)-oxazole hydrochloride (4S)-4-[(1-Methyl-1H-imidazol-4-yl)methyl]-2-(1-methyl-1H-indol-3-yl)-4H, 5H)-oxazole oxalate dihydrate

| TABLE FOR DOSES CONTAINING FROM 1-25 MG OF THE ACTIVE COMPOUND | | | |
|---|---|---|---|
| | Amount-mg | | |
| Active Compound | 1.0 | 2.0 | 25.0 |

-continued

TABLE FOR DOSES CONTAINING FROM 1-25 MG OF THE ACTIVE COMPOUND

| | Amount-mg | | |
|---|---|---|---|
| Microcrystalline cellulose | 49.25 | 48.75 | 37.25 |
| Modified food corn starch | 49.25 | 48.75 | 37.25 |
| Magnesium stearate | 0.50 | 0.50 | 0.50 |

TABLE FOR DOSES CONTAINING FROM 26-100 MG OF THE ACTIVE COMPOUND

| | Amount-mg | | |
|---|---|---|---|
| Active Compound | 26.0 | 50.0 | 100.0 |
| Microcrystalline cellulose | 52.0 | 100.0 | 200.0 |
| Modified food corn starch | 2.21 | 4.25 | 8.5 |
| Magnesium stearate | 0.39 | 0.75 | 1.5 |

All of the active compound, cellulose, and a portion of the corn starch are mixed and granulated to 10% corn starch paste. The resulting granulation is sieved, dried and blended with the remainder of the corn starch and the magnesium stearate. The resulting granulation is then compressed into tablets containing 1.0 mg, 2.0 mg, 25.0 mg, 26.0 mg, 50.0 mg and 100 mg of the active ingredient per tablet.

What is claimed is:

1. A compound of formula I:

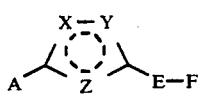

(I)

wherein the broken circle represents one or two double bonds in any position in the 5-membered ring;
One of X and Y independently represents oxygen and the other represents nitrogen or carbon, provided that at least one of X and Y represents oxygen;
Z represents nitrogen;
A represents a group of formula II:

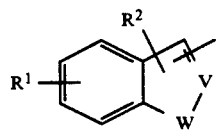

(II)

wherein:
$R^1$ is selected from the group consisting of hydrogen, hydroxy, $C_{1-6}$ alkyl, $C_{2-6}$ alkenyl, $C_{2-6}$ alkynyl, $C_{1-6}$ alkoxy, hydroxy ($C_{1-6}$) alkyl, halogen, amino, cyano, —$CONR^6R^7$ and —$SO_2NR^6R^7$, wherein $R^6$ and $R^7$ are independently selected from the group consisting of hydrogen, $C_{1-6}$ alkyl, $C_{2-6}$ alkenyl and $C_{2-6}$ alkynyl;
$R^2$ is selected from the group consisting of hydrogen, halogen, $C_{1-6}$ alkyl, $C_{1-6}$ alkoxy and $C_{2-6}$ alkylcarbonyl;
V represents nitrogen,

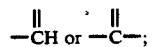

W represents oxygen, sulphur or —$NR^8$, wherein $R^8$ is selected from the group consisting of hydrogen, $C_{1-6}$ alkyl, $C_{2-6}$ alkenyl and $C_{2-6}$ alkynyl;

E represents a bond or a straight or branched alkylene or alkenylene chain containing from 1 to 5 carbon atoms, optionally substituted with hydroxy or phenyl;
F represents an imidazolyl moiety of formula III:

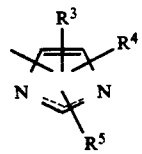

(III)

wherein the broken line represents a bond in one of the two available positions;
$R^3$, $R^4$ and $R^5$ are independently selected from the group consisting of hydrogen, $C_{1-6}$ alkyl, $C_{2-6}$ alkenyl, $C_{2-6}$ alkynyl and aryl selected from the group consisting of phenyl and napthyl and salt thereof.

2. The compound according to claim 1, wherein the ring shown as formula I is a 1,2,4-oxadiazole; oxazole or oxazoline ring.

3. The compound according to claim 1, wherein A represents an indole of formula IIB:

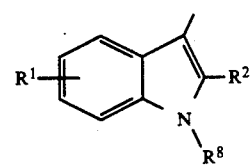

(IIB)

wherein $R^1$, $R^2$ and $R^8$ are as defined in claim 1.

4. The compound according to claim 1 wherein F represents a group of formula IIIA or IIIC:

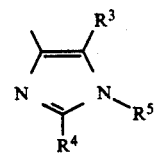

(IIIA)

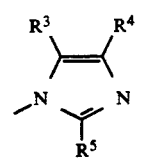

(IIIC)

wherein $R^3$, $R^4$ and $R^5$ are as defined in claim 1.

5. The compound according to claim 1 represented by formula IVA:

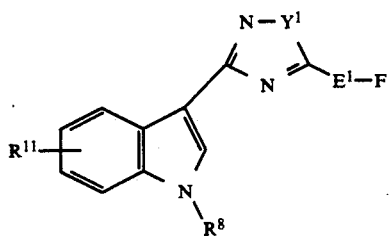

(IVA)

wherein $R^8$ and F are as defined in claim 1; $Y^1$ represent oxygen; $E^1$ represents a group of formula —$(CH_2)_n$— or —CH=CH—, in which n is zero, 1 or 2; and $R^{11}$ is selected from the group consisting of hydrogen, halogen and $C_{1-6}$ alkyl.

6. The compound according to claim 1 represented by formula IVB:

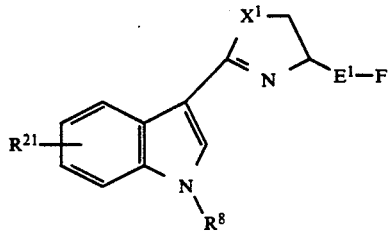

(IVB)

wherein $R^8$ and F are as defined in claim 1; $E^1$ represents a group of formula —$(CH_2)_n$— or —CH=CH—, in which n is zero, 1 or 2; $X^1$ represents oxygen and $R^{21}$ is selected from the group consisting of hydrogen, halogen or $C_{1-6}$ alkyl.

7. The compound according to claim 6, wherein $R^{21}$ is hydrogen; $R^8$ is methyl; $X^1$ is oxygen; $E^1$ is —$CH_2$—; and F represents a group of formula IIIA:

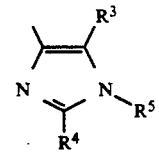

(IIIA)

wherein $R^3$, $R^4$ and $R^5$ are hydrogen.

8. The compound according to claim 1, wherein said compound is selected from the group consisting of 5-(5-methyl-H-imidazol-4-yl)-3-(1-methyl-1H-indol-3-yl)-1,2,4-oxadiazole;

5-[2-(5-methyl-1H-imidazol-4-yl)ethyl]-3-(1-methyl-1H-indol-3-yl)-1,2,4-oxadiazole;

4-[(1H-imidazol-4-yl)methyl]-2-(1-methyl-1H-indol-3-yl)-(4H, 5H)-oxazole;

5-[(1H-imidazol-4-yl)methyl]-3-(1-methyl-1H-indol-3-yl)-1,2,4-oxadiazole;

5-[2-(1H-imidazol-1-yl)ethyl]-3-(1-methyl-1H-indol-3-yl)-1,2,4-oxadiazole;

5-[2-(2-methyl-1H-imidazol-1-yl)ethyl]-3-(1-methyl-1H-indol-3-yl)-1,2,4-oxadiazole;

5-[2-(1H-imidazol-4-yl)ethenyl]-3-(1-methyl-1H-indol-3-yl)-1,2,4-oxadiazole;

4-[(1-methyl-1H-imidazol-4-yl)methyl]-2-(1-methyl-1H-indol-3-yl)-(4H, 5H)-oxazole and salt thereof.

9. A pharmaceutical composition comprising an effective amount of a compound according to claim 1 in association with a pharmaceutically acceptable carrier.

10. A method for treating a patient suffering from a physiological disorder ameliorated by 5HT$_3$ receptor antagonism, said method comprises administering to said patient in need of such treatment a pharmaceutically effective amount of a compound according to claim 1.

* * * * *